United States Patent
Metz et al.

(10) Patent No.: US 8,410,943 B2
(45) Date of Patent: Apr. 2, 2013

(54) BED EXIT LIGHTING

(75) Inventors: Darrell L. Metz, Batesville, IN (US); Jonathan D. Turner, Dillsboro, IN (US); Richard H. Heimbrock, Cincinnati, OH (US); David W. Hornbach, Brookville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 169 days.

(21) Appl. No.: 12/912,320

(22) Filed: Oct. 26, 2010

(65) Prior Publication Data

US 2011/0102181 A1 May 5, 2011

Related U.S. Application Data

(60) Provisional application No. 61/257,132, filed on Nov. 2, 2009.

(51) Int. Cl.
*G08B 23/00* (2006.01)

(52) U.S. Cl. ............... 340/575; 340/573.1; 340/286.07; 340/573.4

(58) Field of Classification Search .................. 340/575, 340/573.1, 573.4, 573.7, 521, 522, 540, 541, 340/686.1, 686.6, 286.07; 315/158; 600/300
See application file for complete search history.

(56) References Cited

U.S. PATENT DOCUMENTS

| 4,700,180 | A  | * | 10/1987 | Vance ........................ 340/573.4 |
| 8,009,042 | B2 | * | 8/2011  | Steiner et al. ................. 340/541 |
| 8,081,083 | B2 | * | 12/2011 | Hinterlong ................. 340/573.4 |
| 2004/0257237 | A1 | * | 12/2004 | Bialecki et al. ............ 340/686.1 |
| 2008/0256445 | A1 |   | 10/2008 | Olch et al. |

FOREIGN PATENT DOCUMENTS

| WO | 2005088192 A1 | 9/2005 |
| WO | 2007056342 A2 | 5/2007 |
| WO | 2009094494 A2 | 7/2009 |
| WO | 2009124397 A2 | 10/2009 |

OTHER PUBLICATIONS

European Search Report for Application No. 10189509.2-1265/ 2316401, dated Aug. 28, 2012, 8 pages.

* cited by examiner

*Primary Examiner* — Anh V La

(74) *Attorney, Agent, or Firm* — Barnes & Thornburg LLP

(57) ABSTRACT

A person-support apparatus includes a frame, a plurality of sensors, and a controller. The plurality of sensors are configured to determine a person's position relative to the frame. The controller is operatively coupled to the sensors. The controller determines whether an exit condition has been met. A light source is operatively coupled to the controller. The light source is activated by the controller when the controller determines that the exit condition has been met.

20 Claims, 6 Drawing Sheets

BED EXIT LIGHTING

CROSS-REFERENCE TO RELATED APPLICATION

This application claims the benefit of U.S. Provisional Patent Application Ser. No. 61/257,132, filed Nov. 2, 2009, which is incorporated herein by reference in its entirety.

BACKGROUND OF THE DISCLOSURE

This disclosure relates generally to a person-support apparatus. More particularly, but not exclusively, one illustrative embodiment relates to a lighting system for assisting a person supported on the person-support apparatus.

A person supported on a person-support apparatus may exit the person-support apparatus occasionally while unsupervised. After exiting the person-support apparatus, the person may bump into equipment and/or fall while moving about the room, which may result in injury to the person and/or damage to the equipment. Incidences of people injuring themselves and/or damaging equipment upon exiting the person-support apparatus may increase in low light or dark conditions. While various systems have been developed, there is still room for development. Thus a need persists for further contributions in this area of technology.

SUMMARY OF THE DISCLOSURE

The present disclosure includes one or more of the features recited in the appended claims and/or the following features which, alone or in any combination, may comprise patentable subject matter.

One illustrative embodiment of the present disclosure includes a person-support apparatus having a control system configured to detect movement of a person on the person-support apparatus and control the operation of a light source upon detection of the person exiting the bed or movement of the person exceeding a predefined movement threshold.

Additional features alone or in combination with any other feature(s), including those listed above and those listed in the claims and those described in detail below, may comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
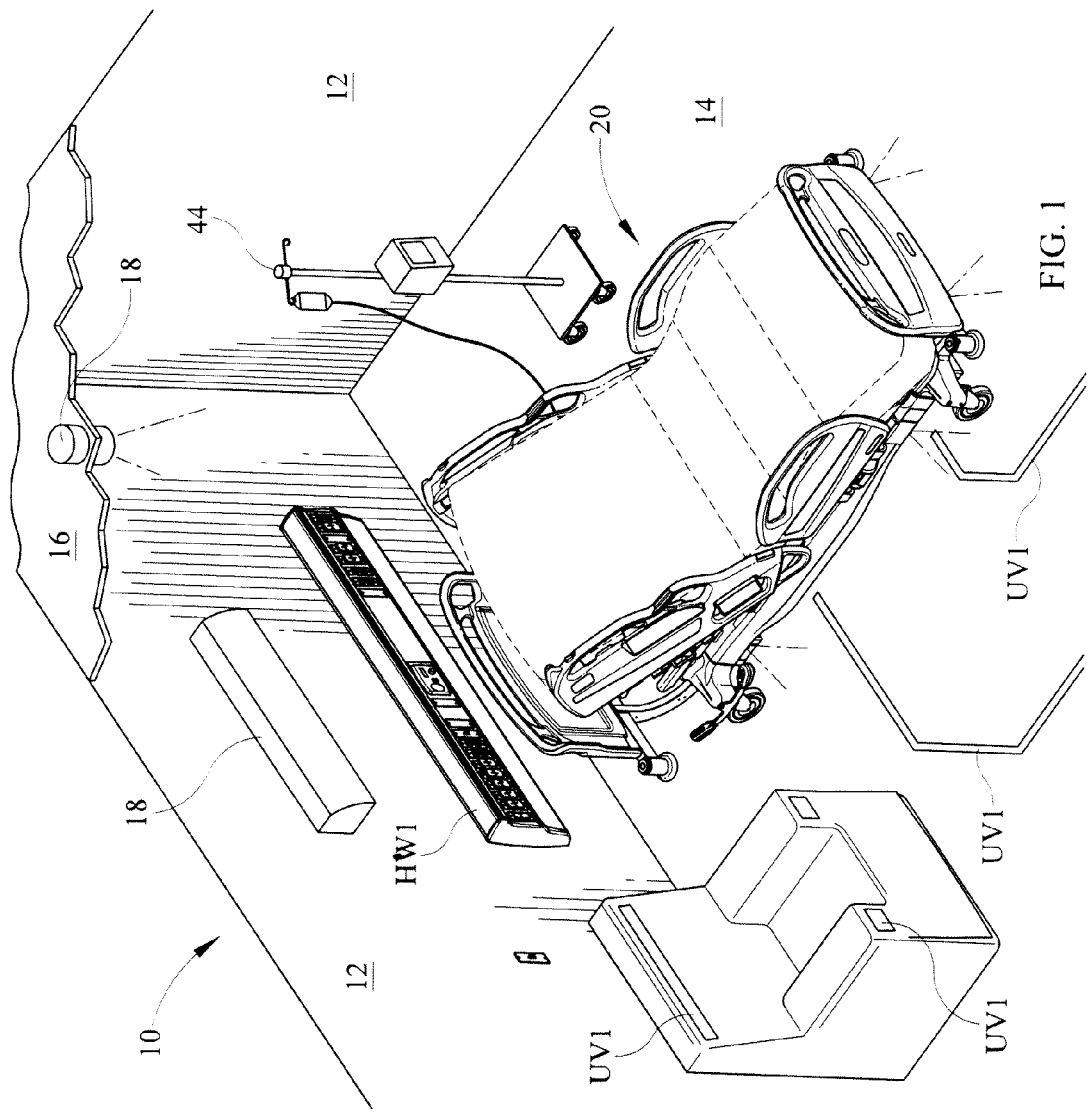
FIG. 1 is an elevated perspective view of a room with a person-support apparatus therein according to one illustrative embodiment of the disclosure.

While inventions described in the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure includes a person-support apparatus having a control system configured to detect movement of a person on the person-support apparatus and control the operation of a light source upon detection of the person exiting the bed or movement of the person exceeding a predefined movement threshold.

A room 10, such as a hospital room 10, has a person-support apparatus 20 positioned therein according to one illustrative embodiment as shown in FIG. 1. The room 10 includes walls 12, a floor 14, a ceiling 16, and a plurality of room lights 18. As shown, the room lights 18 are coupled to and/or integrated into the ceiling 16 and walls 12. Alternatively or in addition, one or more of the room lights 18 may be coupled to and/or integrated into the floor 14, or may be free-standing room lights 18. The light source 18 can also be built into the person-support apparatus 20. The hospital room 10 may include medical devices and equipment, such as a headwall unit HW1, a bed locator (not shown), a service column (not shown), or other equipment that may be coupled to the ceiling 16, walls 12, and/or the floor 14, and which may include room lights 18.

Figure 2:
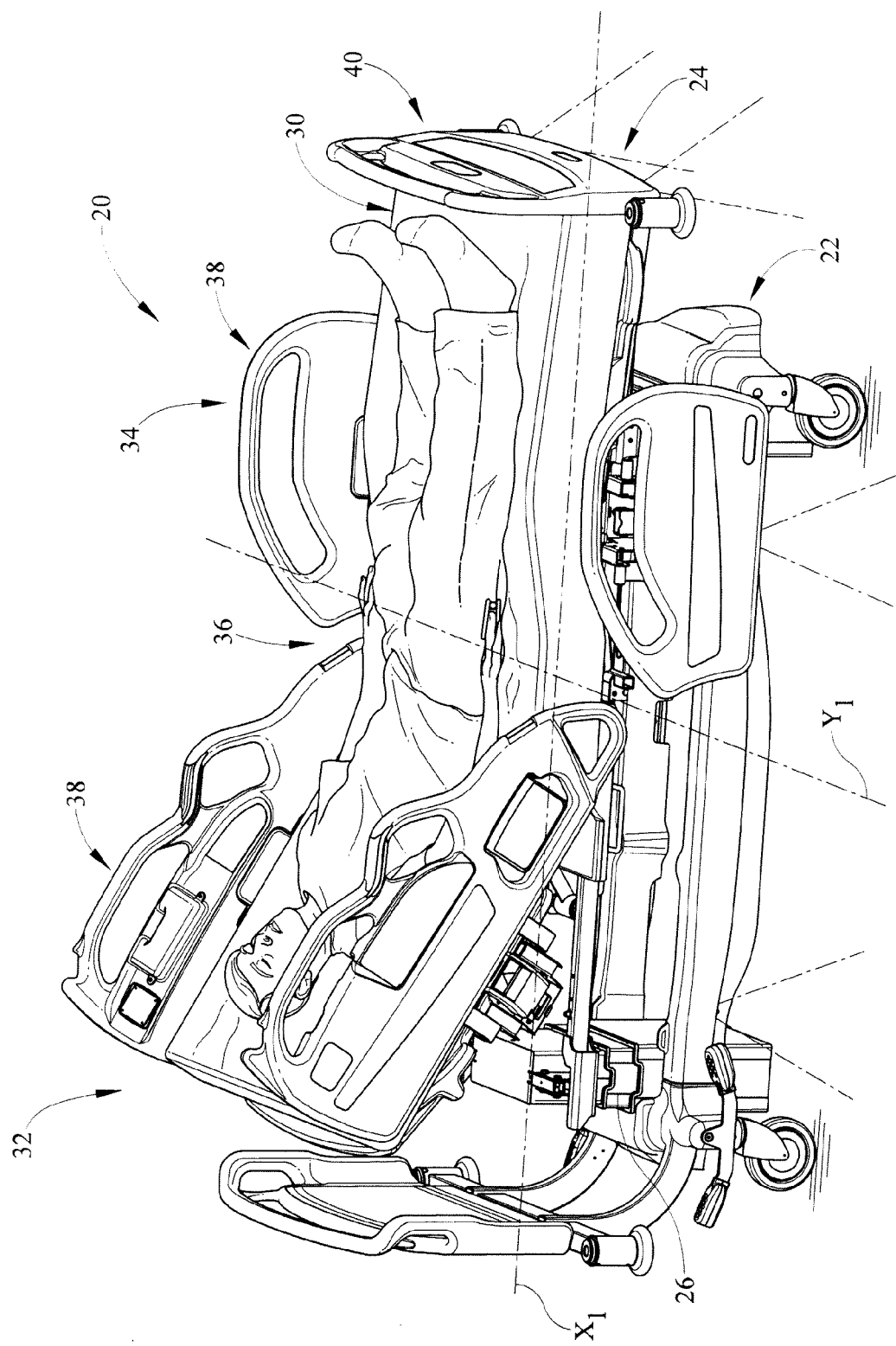
FIG. 2 is a side perspective view of the person-support apparatus of FIG. 1.

In the illustrative embodiment, the person-support apparatus 20 is a hospital bed 20. The bed 20 includes a lower frame or base 22, an upper frame 24, a plurality of supports 26 coupled with the upper frame 24 and the lower frame 22, and a control system 28 as shown in FIGS. 1-5. In other embodiments, the person-support apparatus 20 may be a hospital stretcher or an operating table. In one illustrative embodiment, the person-support apparatus 20 supports a person-support surface 30 on the upper frame 24 as shown in FIGS. 1-2. In this embodiment, the plurality of supports 26 are lift mechanisms that can be configured to move the upper frame 24 with respect to the lower frame 22.

The person-support apparatus 20 includes a head support section 32, where the head of a person (not shown) can be positioned, and a foot support section 34, where the feet of a person (not shown) can be positioned, as shown in FIG. 2. In some embodiments, the person-support apparatus 20 may have a seat support section 36. The head support section 32 is pivotable relative the foot support section 34, so that the person-support apparatus 20 can be articulated between a generally horizontal lying-down position, a reclined position, a sitting position, and an infinite number of intermediate positions therebetween.

The upper frame 24 defines a longitudinal axis X1 that extends at least the length of the person-support apparatus 20 through the head support section 32 and the foot support section 34 along the lateral center of the upper frame 24, and a lateral axis Y1 that is perpendicular to the longitudinal axis X1 and extends at least the width of the person-support apparatus 20 through approximately the longitudinal center of the upper frame 24 as shown in FIG. 2. The upper frame 24 is movable between a Trendelenburg position and a reverse Trendelenburg position. The upper frame 24 includes side rails 38 and end boards 40 as shown in FIG. 2, although these may not be included in other embodiments.

Figure 3:
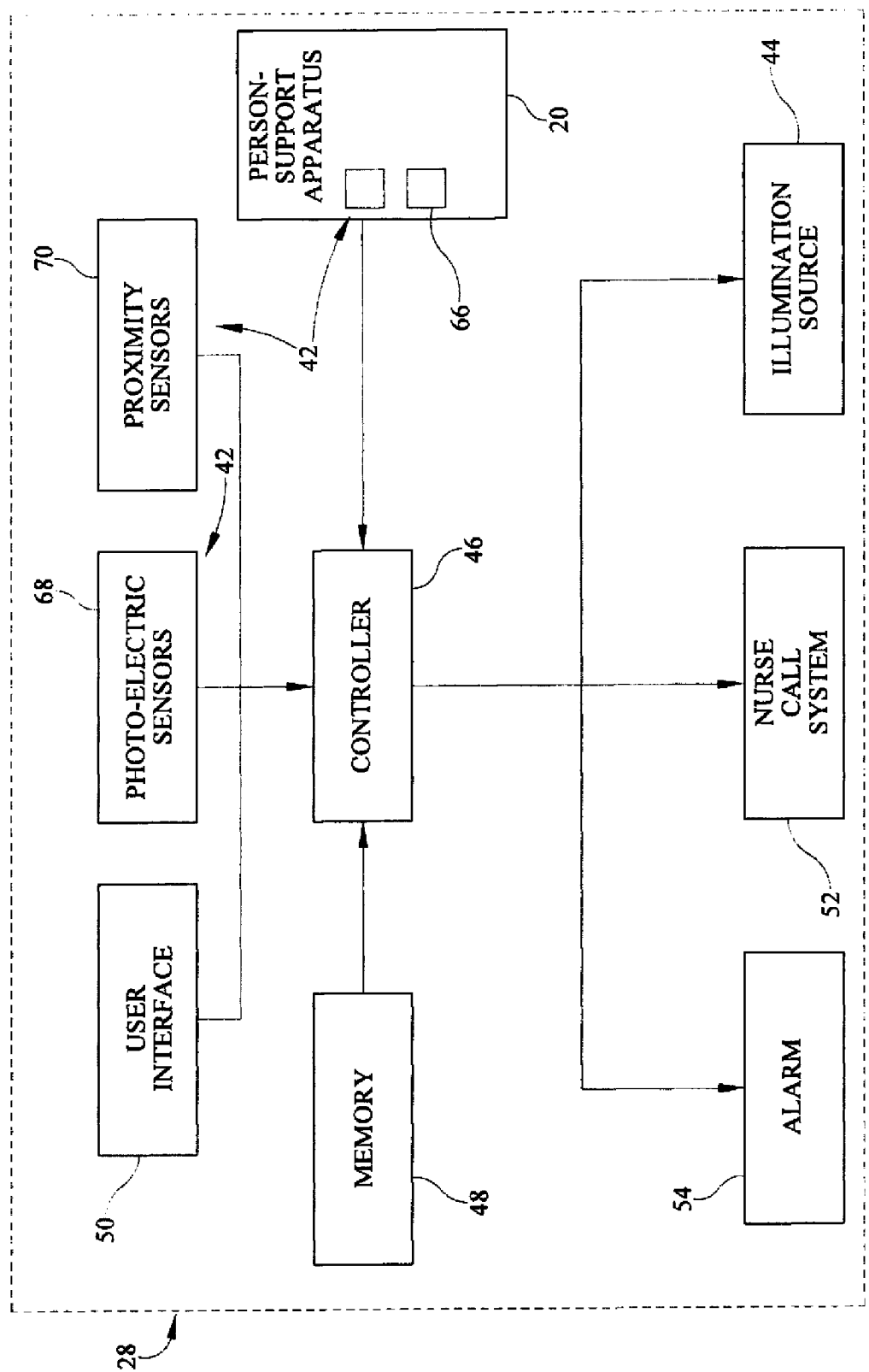
FIG. 3 is a block diagram of the control system of the person-support apparatus of FIG. 1 according to one illustrative embodiment.

The control system 28 includes a plurality of sensors 42, a plurality of light sources 44, a controller 46, and a memory device 48 as shown in FIG. 3. The control system 28 is operably coupled to the person-support apparatus 20. In one illustrative embodiment, a portion of the control system 28 is coupled to the upper frame 24. In another illustrative embodiment, a portion of the control system 28 is integrated into the person-support surface 30. In yet another illustrative embodiment, the control system 28 is remotely located with respect to the person-support apparatus 20. The control system 28 is configured to activate/deactivate the light sources 44 in response to a person supported on the person-support apparatus 20 exiting the person-support apparatus or the person's movements with respect to the person-support apparatus 20 exceeding a predetermined movement threshold. The control system 28 receives an input signal from a user interface 50. Alternatively or in addition, the control system 28 may be configured to receive an input signal from a pendant (not shown). The control system 28 may be configured to send a signal to a nurse call system 52 and/or generate an audio or visual alarm. The control system 28 may be in communication with a hospital network (not shown).

Figure 4:
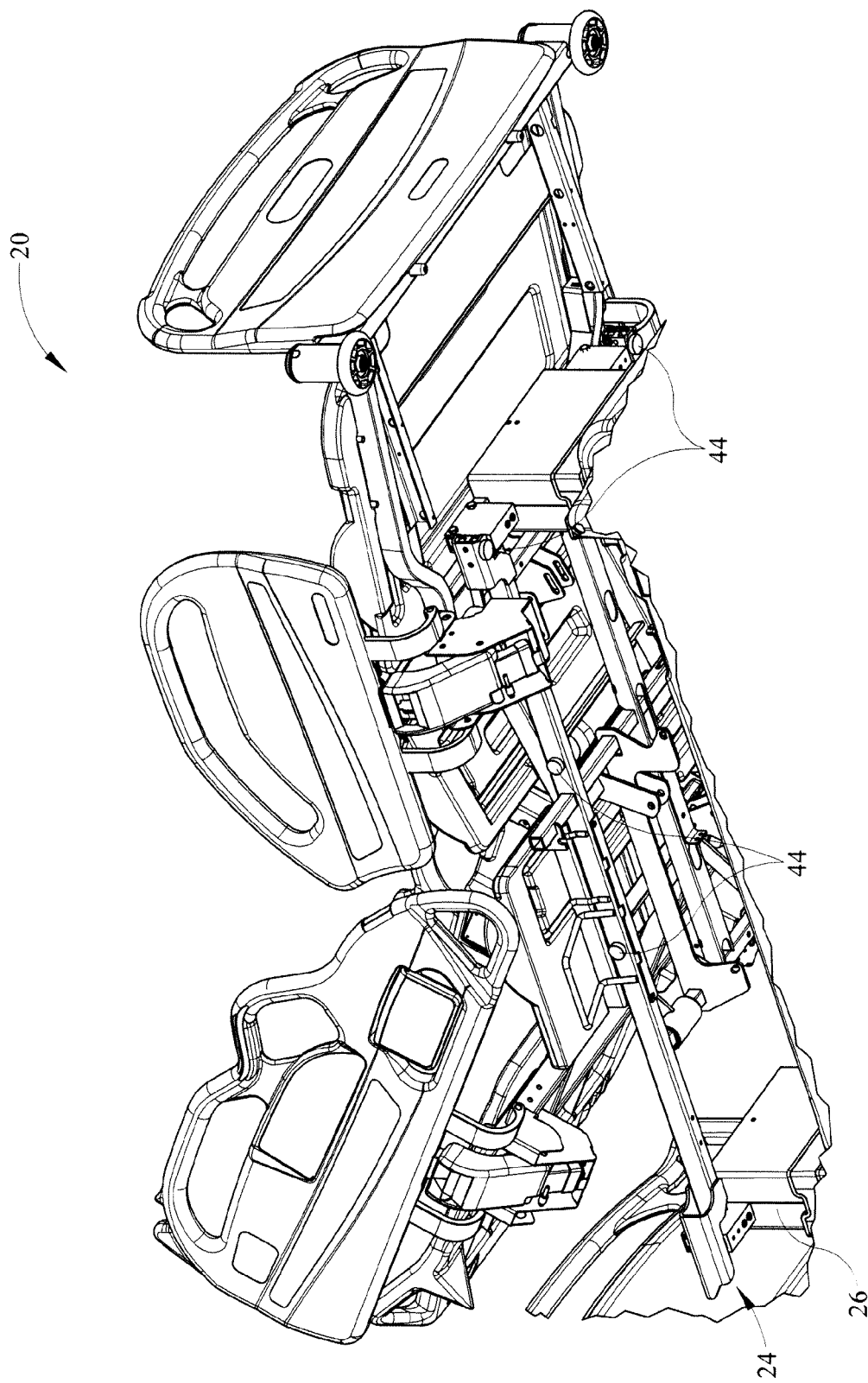
FIG. 4 is a perspective bottom view of the upper frame of the person-support apparatus of FIG. 1 showing a location of the light sources according to one illustrative embodiment.

The light sources 44 are configured to illuminate at least a portion of the room 10 when the controller 46 determines that a person is exiting the person-support apparatus 20 or that the movement of a person supported on the person-support apparatus 20 exceeds a predetermined threshold. In one illustrative embodiment, the light sources 44 are coupled to the underside of the upper frame 24 as shown in FIG. 4. In another illustrative embodiment, the light sources 44 are coupled to a headwall unit HW1 and are operatively coupled to the controller 46 through a connector (not shown), such as, for example, a 72 pin connector. In other illustrative embodiments the light sources 44 may be coupled to at least one of the lower frame 22, the supports 26, a bed locator (not shown), a service column (not shown), a headboard 40, a footboard (not shown), a siderail 38, or other object, surface, or equipment. Alternatively or in addition, the light sources 44 may be coupled or positioned on portable medical equipment, such as an intravenous (IV) pole, that can be coupled to the patient, and can be activated by the control system 28 when the patient exits the person-support apparatus 20, for example, to go to the bathroom as shown in FIG. 1. A user may control the light sources 44 through the user interface 50. The lights 18 and/or light sources 44 may be coupled to a light switch connector (not shown), which may be operatively connected to a light control panel (not shown) in the room and configured to act like a three-way switch wherein the user may activate/deactivate the lights 18 and/or light sources 44.

The light sources 44 may be configured to emit light at different levels of intensity and/or at different wavelengths. The light sources 44 may be configured to emit light at different levels of intensity for a predetermined amount of time, for example, to allow a person's eyes time to adjust to the intensity of the light in the room 10. The light sources 44 may be configured to emit white light and/or colored light. Colored light may be less intense than white light and may help a person's eyes adjust to dark conditions quicker and with less strain. In one illustrative embodiment, the light sources 44 may emit yellow light. In yet another illustrative embodiment, the light sources 44 may emit red light. In yet another embodiment, the light sources 44 may emit a green colored light. The red light may have a wavelength range, for example, of about 620 nm to about 750 nm.

In one illustrative embodiment, the light sources 44 are light emitting diodes (LED's). In another illustrative embodiment, the light sources 44 include an ultraviolet light or black light. The light sources 44 may also be fluorescent lights (compact and/or linear), cold cathode lights, or other lights. Ultraviolet light may be used to illuminate objects UV1, for example, white and/or fluorescent colored objects, so that the objects appear to be glowing in the darkened condition. In one illustrative embodiment, the ultraviolet light is used to illuminate a path outlined by white and/or fluorescent colored strips of tape, paint, or other materials or substances that guide a person to a destination, such as, a washroom or bathroom, in a darkened condition as shown in FIG. 1. The ultraviolet light may also be used to identify obstacles, objects, and/or equipment in the room 10 by marking them with white and/or fluorescent colored strips of tape, paint, or other materials or substances. The ultraviolet light may be used to illuminate any color material or object that the ultraviolet light radiation emitted by the ultraviolet light would prompt the visible effects of fluorescence and phosphorescence.

Figure 5:
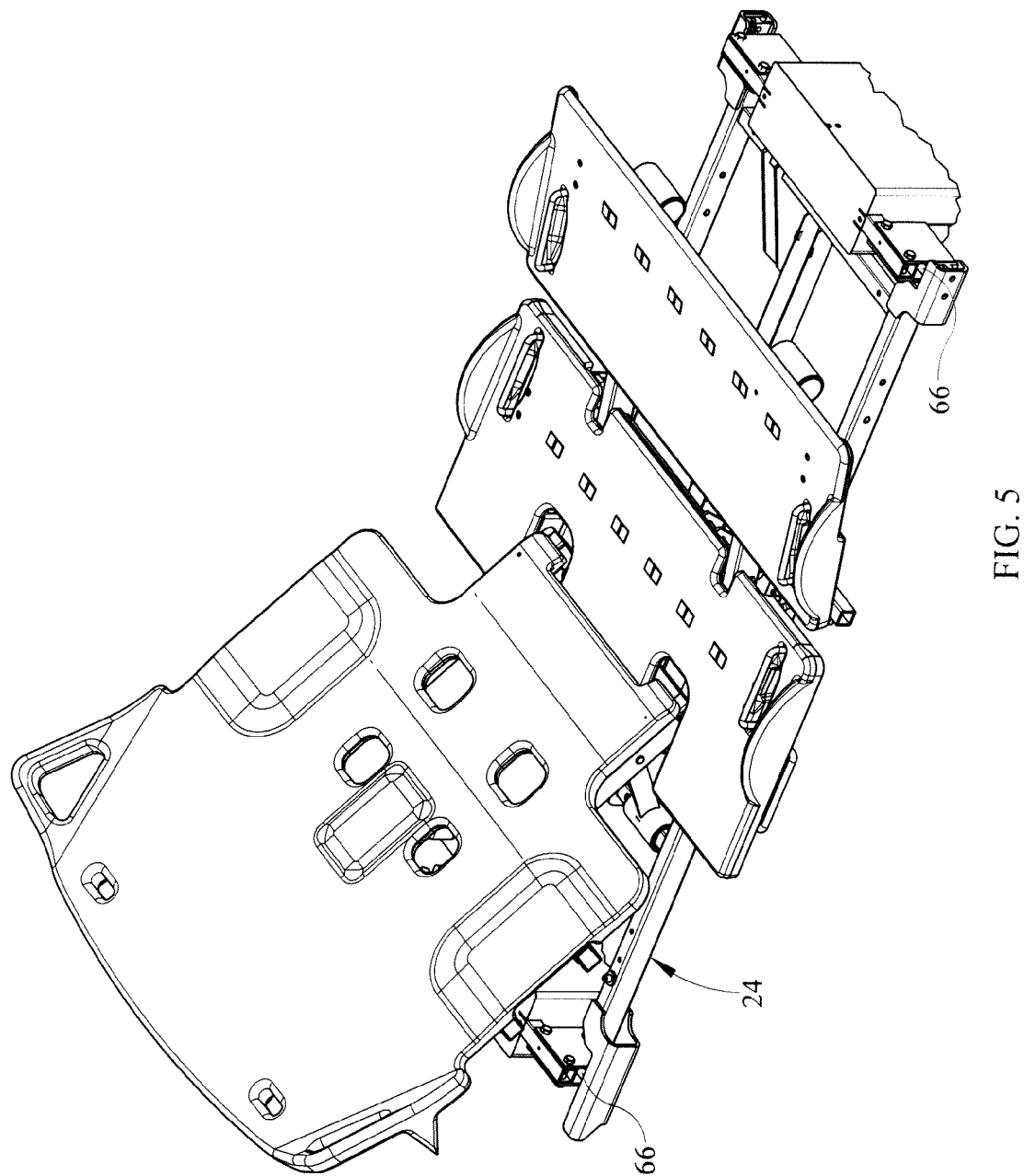
FIG. 5 is a perspective top view of the upper frame of the person-support apparatus of FIG. 1 showing a location of force sensors according to one illustrative embodiment.

The plurality of sensors 42 includes one or more of the force sensors 66, photoelectric sensors 68, and/or proximity sensors 70. The force sensors 66 may be load cells 66 coupled to the upper frame 24 that are configured to sense the amount of force on the upper frame 24 as shown in FIG. 5. The force sensors 66 may include pressure sensors integrated into the person-support surface 30. The force sensors 66 may be coupled to or integrated into the supports 26, lower frame 22, or floor 14. The force sensors 66 generate a load signal that is communicated to the controller 46 corresponding to the presence and/or movement of a person supported on the person-support apparatus 20.

The photoelectric sensors 68 may be coupled to the person-support apparatus 20 or positioned anywhere in the room 10. The photoelectric sensors 68 may be positioned on the person-support apparatus 20 and/or anywhere in the room 10. The photoelectric sensors 68 are configured to detect the intensity of light in the room 10 and generate a signal corresponding thereto. The photoelectric sensors 68 may function as power saving switches that may be configured to prevent the light sources 44 from illuminating when the room 10 is already lit. The photoelectric sensors 68 communicate the intensity signal to the controller 46, which determines whether the intensity of the light in the room 10 is above a predetermined threshold. If the intensity signal is below a predetermined threshold and the controller 46 determines that a person supported on the person-support apparatus 20 is exiting the person-support apparatus 20 or that the person's movements exceed a predetermined movement threshold, the controller 46 activates the light sources 44. If the intensity of the light in the room 10 is above the predetermined threshold and the controller 46 determines that a person supported on the person-support apparatus 20 is exiting the person-support apparatus 20 or that the person's movements exceed a predetermined movement threshold, the controller 46 may not activate the light sources 44, or if the light sources 44 are activated, the controller 46 may deactivate the light sources 44. The intensity of the light emitted by the light sources 44 may be incrementally increased/decreased as a function of the intensity of the light in the room 10.

The proximity sensors 70 may be used to detect the presence of nearby objects without any physical contact. The proximity sensors 70 may be coupled to the person-support apparatus 20 and/or other objects, equipment, and/or surfaces in the room 10. The proximity sensors 70 may be configured to detect the presence of a person in the room 10, such as a caregiver, and may generate a proximity signal. If the proximity sensors 70 detect a caregiver, the controller 46 may not activate the light sources 44. If the proximity sensors 70 do not detect a caregiver, the controller 46 may activate the light sources 44 upon determining that the intensity signal is below a predetermined threshold and that the person supported on the person-support apparatus 20 is exiting the person-support apparatus 20 or the person's movements exceed a predetermined movement threshold.

The controller 46 is operatively coupled to the memory devices 44, the illumination sources 44, and the sensors 42. The controller 46 may communicate wirelessly with the memory devices 44, the light sources 44, and the sensors 42. The controller 46 is configured to receive an input signal from at least one of the plurality of sensors 42. The controller 46 includes control logic 54 stored in memory device 48. The control logic 54 may cause the controller 46 to activate/deactivate the illumination sources 44 and/or increase/decrease the intensity of the light as a function of the input signal received from at least one of the plurality of sensors 42.

In one illustrative embodiment, the control logic 54 is configured to monitor patient movement relative to a reference load cell 66 distribution, impending exit from the person-support surface 30 and/or exit therefrom. In one illustrative embodiment, the operating logic 54 executes such functions in the form of a combined flowchart and/or state machine. The operating logic 54 may be executed periodically by the controller 46, e.g., once every 200 ms, to monitor patient movement relative to a reference load cell 66 distribution, impending exit from the person-support surface 30. The operating logic 54 may begin with the controller 46 determining whether the person position monitor module is armed, i.e., whether one of the patient monitoring modes was active, before the last power down of the person position monitor module.

The patient monitoring modes may include a patient movement (PM) mode wherein the person position monitor module is operable to monitor movement of a patient on the person-support surface 30 by monitoring weight distribution among two or three of the four load cells 66 relative to a predefined set of PM load cell threshold data, a patient exit (PE) mode wherein the person position monitor module is operable to monitor impending exit from the person-support surface 30 by monitoring weight distribution of the four load cells 66 relative to a predefined set of PE load cell threshold data, and a patient out-of-bed (POOB) mode wherein the person position monitor module is operable to monitor exit of the patient from the person-support surface 30 by monitoring the patient weight distributed over the four load cells 66 relative to an armed patient weight, wherein the armed weight corresponds to the patient weight distributed over the four load cells 66 when the patient monitoring mode was armed as will be described in greater detail hereinafter. The person position monitor module may be integrated into the person-support surface 30. If the controller 46 determines that the person position monitor module was not armed before the last system power down, execution of the operating logic 54 causes the controller 46 to execute a state machine preparation routine. If the controller 46 instead determines that the person position monitor module was armed before the last system power down, execution of the operating logic 54 advances to an Arming From Power Up Transition State of the state machine where the patient weight is processed to determine whether it is contained within a defined armed range prior to advancing to the PM Active State of the state machine to resume operation of the patient monitoring mode that was active at the last system power down. One example of such a system can be found in U.S. Pat. No. 7,253,366 to Bhai, issued on Aug. 7, 2007.

In another illustrative embodiment, the controller 54 detects the ingress/egress of a person to/from the person-support apparatus 20 by determining the center of gravity of the weight thereon. One example of such a system can be found in U.S. Pat. No. 5,276,432 to Travis, issued on Jan. 4, 1994. In still another illustrative embodiment, the controller 54 treats the upper frame 24 as though it were disposed within a horizontal plane, extracts from the weight value measured by each load cell 66 a portion which represents the weight of a patient, uses the extracted portions to calculate the location within the plane of a center of gravity of the patient, determines whether the location of the center of gravity is inside or outside a predetermined region which is a portion of the plane, and initiates an alarm when it is found that the center of gravity is located outside the predetermined region. One example of such a system can be found in U.S. Pat. No. 5,276,432 to Travis, issued on Jan. 4, 1994.

Figure 6:
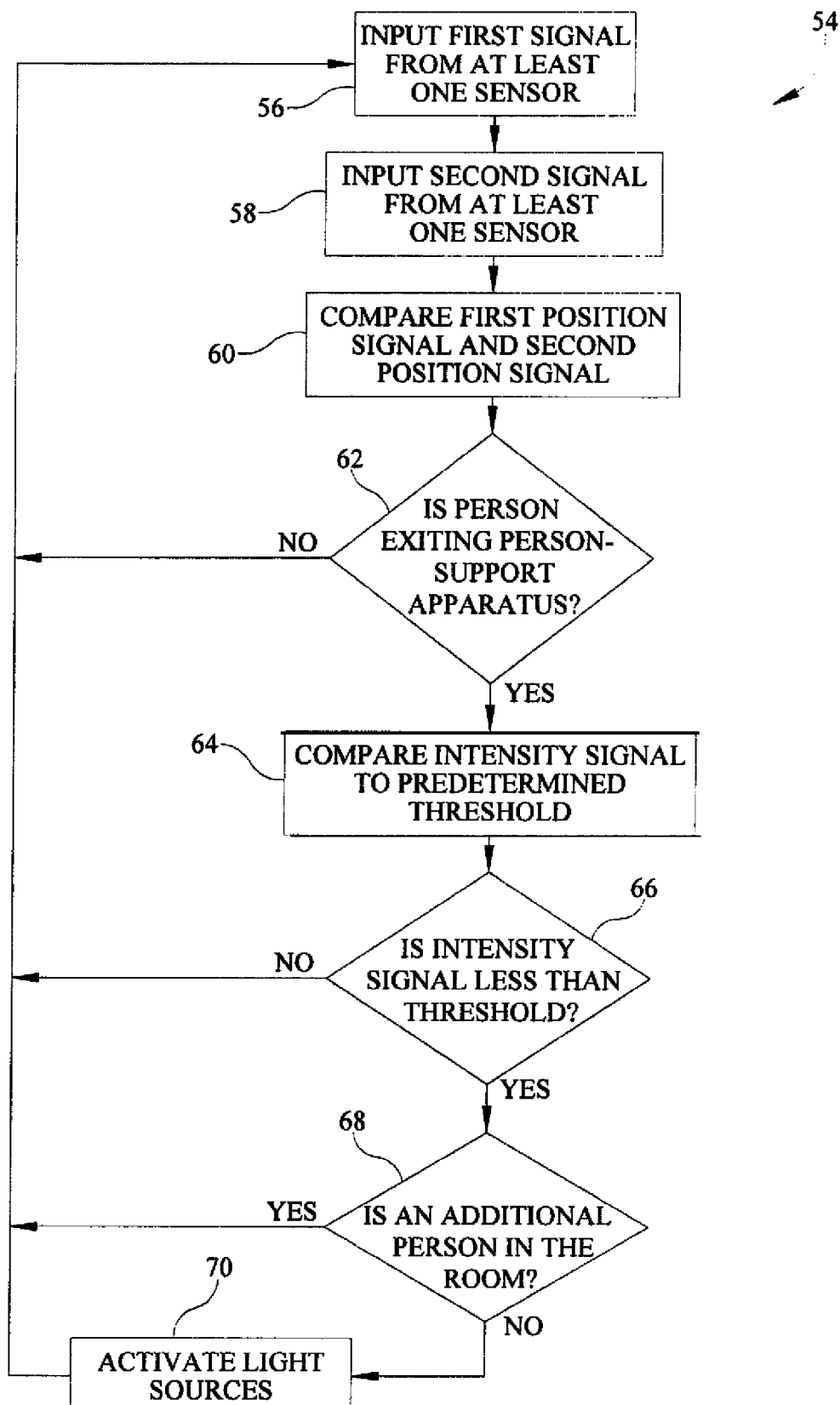
FIG. 6 is a flowchart illustrating a control logic according to one illustrative embodiment configured to be executed by the control system of FIG. 3.

In still another illustrative embodiment, the control logic 54 operates as shown in FIG. 6. The control logic 54 includes operations/conditionals 56, 58, 60, 62, 64, 66, 68, and 70. The control logic begins with operation 56 in which the controller 46 receives a first input signal from at least one of the plurality of sensors 42 indicative of the position of a person supported on the person-support apparatus 20 with respect to the person-support apparatus 20. The controller 46 stores the first input signal in the memory 48.

In operation 58 the controller 46 receives a second set of input signals from at least one of the plurality of sensors 42. The second input signal is indicative of the position of a person supported on the person-support apparatus 20 with respect to the person-support apparatus 20, the intensity of light in the room 10, and whether a caregiver is in the room 10. The first input signal may also be a set of inputs indicative of the position of a person supported on the person-support apparatus 20 with respect to the person-support apparatus 20, the intensity of light in the room 10, and whether a caregiver is in the room 10.

In operation 60, the controller 46 compares the first input signal indicative of the position of the person with respect to the person-support apparatus 20 with the corresponding second input signal to determine if the person appears to be exiting the person-support apparatus 20 or the person's movement exceeds a predetermined movement threshold.

In conditional 62, if the controller 46 determines that the person is not exiting the person-support apparatus 20 or the person's movement does not exceed the predetermined movement threshold, then the control logic 54 returns to operation 56. If the controller 46 determines that the person is exiting the person-support apparatus 20 or the person's movement exceeds the predetermined movement threshold, then the control logic 54 proceeds to operation 64.

In operation 64, the controller 46 compares the second input indicative of the intensity of the light in the room 10 to the corresponding predetermined threshold level to determine if the light sources 44 should be activated.

In conditional 66, if the second input is greater than the threshold level, the controller 46 may not activate the light sources 44, or may deactivate the light sources 44 if they are already activated, and may return to operation 56. If the second input is less than the threshold level, the controller 46 proceeds to operation 68.

In conditional 68, the controller 46 checks the second input indicative of whether another person is in the room 10. If the controller 46 determines that another person is in the room 10, the controller 46 returns to operation 56. If the controller 46 determines that another person, such as a caregiver, is not in the room 10, then the controller 46 proceeds to operation 70.

In operation 70, the controller activates the illumination sources 44 and/or increases the intensity of the light produced by the light sources 44.

In operation, the sensors 42 sense at least one of the position of a person on the person-support surface 30 with respect to the support surface 30, the intensity of the light in the room 10, and whether a caregiver is in the room 10 and generate an input signal corresponding thereto. The input signals are communicated to the controller 46, which determines whether or not to activate the light sources 44. If the controller 46 determines that the intensity of the light in the room 10 is below a predetermined threshold and a person supported on the person-support apparatus 20 is exiting the person-support apparatus 20 or that the person's movements exceed a predetermined movement threshold, the controller 46 activates the light sources 44. If the controller 46 determines that the intensity of the light in the room 10 is above a predetermined threshold and a person supported on the person-support apparatus 20 is exiting the person-support apparatus 20 or that the person's movements exceed a predetermined movement threshold, the controller 46 may not activate the light sources 44 or may deactivate the light sources 44 if they were already activated. The controller 46 may maintain the activation of the light sources 44 for a predetermined amount of time after the movement no longer exceeds the predetermined movement threshold or the person returns to the person-support apparatus 20 and is supported thereon. The controller 46 may dim the light sources 44 from an activated state to a deactivated state or raise the intensity of the light sources 44 from a deactivated state to an activated state incrementally over a predetermined amount time to allow for the person's eyes to adjust to the intensity of the light in the room.

There are many aspects of the present disclosure. According to one aspect, a person-support apparatus includes a frame; a plurality of sensors including a first sensor configured to sense an amount of force on the frame and generate a corresponding force signal, and a second sensor configured to detect an intensity of light and generate a corresponding intensity signal. The person-support apparatus also includes a controller operatively coupled to the plurality of sensors. The controller is configured to receive the force signal, determine whether an exit condition has been met and receive the intensity signal. A light source is configured to illuminate an area adjacent the frame. The light source is operatively coupled to the controller. The light source is activated by the controller when the controller determines that the exit condition has been met and the controller determines, based on the intensity signal, that the light source may be activated.

The frame may include a lower portion, an upper portion, and at least one support member movably supporting the upper portion above the lower portion. The light source may be coupled to at least a portion of the upper portion of the frame.

The exit condition may be at least one of a person that was supported on the frame no longer being supported on the frame and a person supported on the frame moving with respect to the frame such that a movement threshold is exceeded. The light source may emit at least one of ultraviolet light and visible light. The light source may emit ultraviolet light that illuminates indicators in the room. The indicators may be configured to exhibit visual effects when illuminated with ultraviolet light to identify at least one of a location of an object and a path from a first location to a second location.

The light source may be configured to emit light at varying intensities. The light source may be coupled to a medical device. The light source may be a room light.

One or more of the sensors may be configured to sense the intensity of the ambient light in the room and generate an intensity signal corresponding thereto. The controller may be configured to one of activate and deactivate the light source if the intensity signal is one of below and above a predetermined threshold, respectively.

The controller may be in communication with a nurse call system. The controller may be in communication with a user interface configured to receive an input from a user. The light source may be at least one of activated and deactivated in response to the input from the user.

One or more of the sensors may be configured to sense when a person other than the person supported on the person-support apparatus is present in the room and generate an additional person signal corresponding thereto. The controller may be configured to one of activate and deactivate the light source if the additional person signal indicates an additional person is one of not present and present in the room, respectively. One or more of the sensors may be integrated into a person-support surface supported on the frame. The controller may communicate wirelessly with at least one of the light source and the plurality of sensors. A status indicator may be configured to at least one of audibly and visually indicate the status of the at least one of the person supported on the person-support apparatus and the person-support apparatus.

According to another aspect, a person-support apparatus includes a frame configured to support a person in at least a horizontal position, a first sensor configured to generate a position signal indicative of a person's position relative to the person-support apparatus, a second sensor configured to sense a light intensity in an area adjacent the person support apparatus and generate a corresponding intensity signal, a third sensor configured to detect the presence of a person in the area adjacent the person-support apparatus and generate a corresponding proximity signal, and a controller operatively coupled to the first, second, and third sensors. The controller is configured to receive the position signal and determine whether an exit condition has been met, receive the intensity signal and determine whether an intensity condition has been met, and receive the proximity signal and determine whether a proximity condition has been met. A light source is in communication with the controller. The light source is configured to illuminate at least a portion of the area adjacent the person-support apparatus. The light source is activated by the controller when the controller determines that the exit condition has been met and the intensity condition has been met and the proximity condition has been met.

The person-support apparatus may include a device positioned within a room the person-support apparatus is located in and configured to be movable independent of the person-support apparatus; wherein the light source is coupled to the device. The device may be configured to be removably coupled to the person-support apparatus. The device may be at least one of portable medical equipment and architectural medical equipment.

The controller may be configured to activate the light source at different levels of intensity for predetermined amounts of time.

According to another aspect, a person-support apparatus includes a frame, a plurality of sensors configured to sense an amount of force on the frame and generate a corresponding force signal, and a controller operatively coupled to the plurality of sensors. The controller is configured to receive the force signals and determine whether an exit condition has been met. The person-support apparatus also includes a status indicator configured to indicate the status of at least one of a person supported on the person-support apparatus and the person-support apparatus, and a light source operatively coupled to the controller. The light source is activated by the controller when the controller determines that the exit condition has been met.

The frame may include a lower portion, an upper portion, and at least one support member movably supporting the upper portion above the lower portion. The light source may be coupled to at least a portion of the upper portion of the frame.

The exit condition may be at least one of a person that was supported on the frame no longer being supported on the frame and a person supported on the frame moving with respect to the frame such that a movement threshold is exceeded.

The light source may emit at least one of ultraviolet light and visible light. The light source may emit ultraviolet light that illuminates indicators in the room. The indicators may be configured to exhibit visual effects when illuminated with ultraviolet light to identify at least one of a location of an object and a path from a first location to a second location. The light source may be configured to emit light at varying intensities. The light source may be coupled to a medical device. The light source may be a room light.

One or more of the sensors may be configured to sense the intensity of the ambient light in the room and generate an intensity signal corresponding thereto. The controller may be configured to one of activate and deactivate the light source if the intensity signal is one of below and above a predetermined threshold, respectively.

The controller may be in communication with a nurse call system. The controller may be in communication with a user interface configured to receive an input from a user. The light source may be at least one of activated and deactivated in response to the input from the user.

One or more of the sensors may be configured to sense when a person other than the person supported on the person-support apparatus is present in the room and generate an additional person signal corresponding thereto. The controller may be configured to one of activate and deactivate the light source if the additional person signal indicates an additional person is one of not present and present in the room, respectively.

One or more of the sensors may be integrated into a person-support surface supported on the frame. The controller may communicate wirelessly with at least one of the light source and the plurality of sensors. The status indicator may be configured to at least one of audibly and visually indicate the status of the at least one of the person supported on the person-support apparatus and the person-support apparatus.

According to another aspect, a method includes sensing a first force on a person-support apparatus with at least one sensor and generating a first force signal corresponding thereto; sensing a second force on a person-support apparatus with the at least one sensor and generating a second force signal corresponding thereto; comparing the first force signal and the second force signal to determine if an exit condition has been met; and activating an light source in response to the exit condition being met, wherein the light source is not configured to indicate the status of at least one of a person supported on the person-support apparatus and the person-support apparatus.

The exit condition may be at least one of a person that was supported on the person-support apparatus no longer being supported on the person-support apparatus and a person supported on the person-support apparatus moving with respect to the person-support apparatus such that a movement threshold is exceeded.

The light source may emit at least one of ultraviolet light and visible light. The light source may emit ultraviolet light that illuminates indicators in the room. The indicators may be configured to exhibit visual effects when illuminated with ultraviolet light to identify at least one of a location of an object and a path from a first location to a second location. The light source may be configured to emit light at varying intensities.

The method may include sensing an intensity of ambient light in the room with at least one sensor and generating an intensity signal corresponding thereto; comparing the intensity signal to a predetermined intensity threshold; and one of activating and deactivating the light source if the intensity signal is one of below and above the predetermined intensity threshold, respectively.

The method may include sensing when a person other than a person supported on the person-support apparatus is in the room with at least one sensor and generating an additional person signal corresponding thereto; and one of activating and deactivating the light source if the controller determines that an additional person is one of not present and present, respectively.

According to yet another aspect, a kit for upgrading a safety system of a person-support apparatus including a controller operatively coupled to a memory device includes a light source wherein the light source is not configured to indicate the status of at least one of a person supported on the person-support apparatus and the person-support apparatus. The kit also includes a connector configured to facilitate electrical communication between the controller and the light source, and a media storage device storing instructions thereon. The media storage device is configured to communicate the instructions to the controller to be stored on the memory device. The instructions cause the controller to activate the light source if an exit condition is met.

The person-support apparatus may include a frame with a lower portion, an upper portion, and at least one support member movably supporting the upper portion above the lower portion. The light source may be coupled to at least a portion of the upper portion of the frame.

The instruction set may be configured to cause the controller to receive a first force signal corresponding to a first force exerted on the person-support apparatus from a sensor, receive a second force signal corresponding to a second force exerted on the person-support apparatus from the sensor, compare the first force signal and the second force signal to determine if an exit condition is met, and activate the light source if the exit condition is met.

The exit condition may be at least one of a person that was supported on the person-support apparatus no longer being supported on the person-support apparatus and a person supported on the person-support apparatus moving with respect to the person-support apparatus such that a movement threshold is exceeded.

The light source may emit at least one of visible light and ultraviolet light. The light source may be configured to emit light at varying intensities.

The kit may include one or more sensors configured to sense the intensity of the ambient light in the room and generate an intensity signal corresponding thereto.

The instruction set may be configured to cause the controller to receive the intensity signal, compare the intensity signal to a predetermined intensity threshold, and one of activate and deactivate the light source if the intensity signal is one of below and above the predetermined intensity threshold, respectively.

The kit may include one or more sensors configured to sense when a person other than the person supported on the person-support apparatus is present in a room the person-support apparatus is located in and generate an additional person signal corresponding thereto.

The instruction set may be configured to cause the controller to receive the additional person signal and one of activate and deactivate the light source if an additional person is one of not present and present in the room, respectively. The connector may be a wireless communication device.

According to another aspect, a person-support apparatus includes a frame, a plurality of sensors configured to sense an amount of force on the frame and generate a corresponding force signal, and a controller operatively coupled to the plurality of sensors. The controller is configured to receive the force signals and determine whether an exit condition has been met. A light source is operatively coupled to the controller. The light source is activated by the controller when the controller determines that the exit condition has been met. The light source is not configured to indicate a status of at least one of a person supported on the person-support apparatus and the person-support apparatus.

According to another aspect, a system includes a person-support apparatus including a frame, a plurality of sensors configured to sense an amount of force on the frame and generate a corresponding force signal, and a controller operatively coupled to the plurality of sensors. The controller is configured to receive the force signals and determine whether an exit condition has been met. A device is positioned within a room in which the person-support apparatus is located and configured to be movable independent of the person-support apparatus. A light source is coupled to the device and in communication with the controller. The light source is activated by the controller when the controller determines that the exit condition has been met.

The device may be configured to be removably coupled to the person-support. The device may be at least one of portable medical equipment and architectural medical equipment.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described may be desirable, it nonetheless may not be necessary and embodiments lacking the same are contemplated as being within the scope of this disclosure.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item may include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations will be apparent to those skilled in the art. Also, while multiple inventive aspects and principles have been presented, they need not be utilized in combination, and various combinations of inventive aspects and principles are possible in light of the various embodiments provided above.

What is claimed is:

1. A person-support apparatus, comprising:
a frame;
a plurality of sensors including a first sensor configured to sense an amount of force on the frame and generate a corresponding force signal, and a second sensor configured to detect an intensity of light and generate a corresponding intensity signal;
a controller operatively coupled to the plurality of sensors, the controller being configured to receive the force signal, determine whether an exit condition has been met and receive the intensity signal; and
a light source configured to illuminate an area adjacent the frame, the light source being operatively coupled to the controller, the light source being activated by the controller when the controller determines that the exit condition has been met and the controller determines, based on the intensity signal, that the light source may be activated.

2. The person-support apparatus of claim 1, wherein the frame includes a lower portion, an upper portion, and at least one support member movably supporting the upper portion above the lower portion, and the light source is coupled to at least a portion of the upper portion of the frame.

3. The person-support apparatus of claim 1, wherein the exit condition is at least one of a person that was supported on the frame no longer being supported on the frame and a person supported on the frame moving with respect to the frame such that a movement threshold is exceeded.

4. The person-support apparatus of claim 1, wherein the light source emits at least one of ultraviolet light and visible light.

5. The person-support apparatus of claim 1, wherein the light source emits ultraviolet light that illuminates indicators in the room, the indicators are configured to exhibit visual effects when illuminated with ultraviolet light to identify at least one of a location of an object and a path from a first location to a second location.

6. The person-support apparatus of claim 1, wherein the light source is configured to emit light at varying intensities.

7. The person-support apparatus of claim 1, wherein the light source is coupled to a medical device.

8. The person-support apparatus of claim 1, wherein the light source is a room light.

9. The person-support apparatus of claim 1, wherein at least one of the plurality of sensors is configured to sense the intensity of the ambient light in the room and generate an intensity signal corresponding thereto, the controller is configured to one of activate and deactivate the light source if the intensity signal is one of below and above a predetermined threshold, respectively.

10. The person-support apparatus of claim 1, wherein the controller is in communication with a nurse call system.

11. The person-support apparatus of claim 1, wherein the controller is in communication with a user interface configured to receive an input from a user, the light source being at least one of activated and deactivated in response to the input from the user.

12. The person-support apparatus of claim 1, wherein at least one of the plurality of sensors is configured to sense when a person other than the person supported on the person-support apparatus is present in the room and generate an additional person signal corresponding thereto, the controller is configured to one of activate and deactivate the light source if the additional person signal indicates an additional person is one of not present and present in the room, respectively.

13. The person-support apparatus of claim 1, wherein at least one of the plurality of sensors is integrated into a person-support surface supported on the frame.

14. The person-support apparatus of claim 1, wherein the controller communicates wirelessly with at least one of the light source and the plurality of sensors.

15. The person-support apparatus of claim 1, comprising a status indicator configured to at least one of audibly and visually indicate the status of the at least one of the person supported on the person-support apparatus and the person-support apparatus.

16. A person-support apparatus, comprising:
- a frame configured to support a person in at least a horizontal position;
- a first sensor configured to generate a position signal indicative of a person's position relative to the person-support apparatus,
- a second sensor configured to sense a light intensity in an area adjacent the person support apparatus and generate a corresponding intensity signal;
- a third sensor configured to detect the presence of a person in the area adjacent the person-support apparatus and generate a corresponding proximity signal;
- a controller operatively coupled to the first, second, and third sensors, the controller being configured to receive the position signal and determine whether an exit condition has been met, receive the intensity signal and determine whether an intensity condition has been met, and receive the proximity signal and determine whether a proximity condition has been met; and
- a light source in communication with the controller, the light source being configured to illuminate at least a portion of the area adjacent the person-support apparatus, the light source being activated by the controller when the controller determines that the exit condition has been met and the intensity condition has been met and the proximity condition has been met.

17. The person-support apparatus of claim 16, comprising a device positioned within a room the person-support apparatus is located in and configured to be movable independent of the person-support apparatus; wherein the light source is coupled to the device.

18. The person-support apparatus of claim 17, wherein the device is configured to be removably coupled to the person-support apparatus.

19. The person-support apparatus of claim 17, wherein the device is at least one of portable medical equipment and architectural medical equipment.

20. The person-support apparatus of claim 16, wherein the controller is configured to activate the light source at different levels of intensity for predetermined amounts of time.

* * * * *